United States Patent [19]

Lawson

[11] Patent Number: 5,847,158
[45] Date of Patent: Dec. 8, 1998

[54] PROCESS FOR PREPARING 2,4-DIOXO-3-AZABICYCLO[3.1.0]HEXANES

[75] Inventor: Nicholas John Lawson, Sandwich, United Kingdom

[73] Assignee: Pfizer Inc., New York, N.Y.

[21] Appl. No.: 878,909

[22] Filed: Jun. 19, 1997

[30] Foreign Application Priority Data

Jul. 9, 1996 [GB] United Kingdom ............... 9614422

[51] Int. Cl.$^6$ .................... C07D 209/38; C07D 225/00
[52] U.S. Cl. .................................. 548/513; 540/450
[58] Field of Search ....................... 548/513; 540/450

[56] References Cited

U.S. PATENT DOCUMENTS 5,298,629  3/1994  Braish ..................................... 548/452

FOREIGN PATENT DOCUMENTS 9318001  9/1993  WIPO .
9519361  7/1995  WIPO .

OTHER PUBLICATIONS

March, "Advanced Organic Chemistry—Reactions, Mechanisms, and Structure." 4th Edition, 1992, pp. 362–363.

Primary Examiner—Mukund J. Shah
Assistant Examiner—Tamthom T. Ngo
Attorney, Agent, or Firm—Peter C. Richardson; Paul H. Ginsburg; Gezina Holtrust

[57] ABSTRACT

A process for preparing a compound of formula (I):

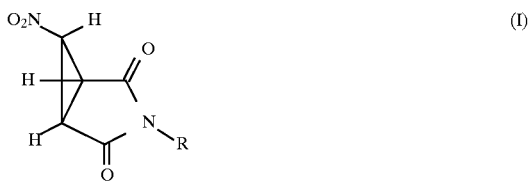

wherein R is $C_1$–$C_6$ alkyl, $C_3$–$C_6$ cycloalkyl or benzyl, and wherein the phenyl moiety of said benzyl group is optionally substituted with one or two substituents each independently selected from halo, nitro, $C_1$–$C_6$ alkyl, $C_1$–$C_6$ alkoxy, amino and trifluoromethyl, which comprises treating a solution of a compound of formula (II):

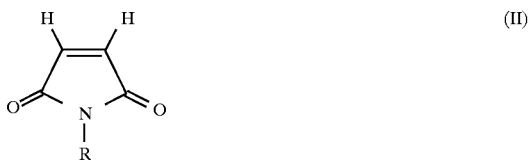

wherein R is as defined for formula (I), and a halonitromethane in a first organic solvent, with a quaternary ammonium fluoride of formula (III):

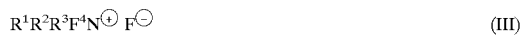

wherein $R^1, R^2, R^3$ and $R^4$ are each independently selected from $C_1$–$C_8$ alkyl and benzyl, optionally in solution in a second organic solvent.

20 Claims, No Drawings

PROCESS FOR PREPARING 2,4-DIOXO-3-AZABICYCLO[3.1.0]HEXANES

This invention relates to a process for preparing an exo-compound of formula (I):

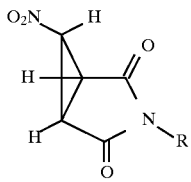

wherein R is $C_1$–$C_6$ alkyl, $C_3$–$C_6$ cycloalkyl or benzyl, and wherein the phenyl moiety of said benzyl group is optionally substituted with one or two substituents each independently selected from halo, nitro, $C_1$–$C_6$ alkyl, $C_1$–$C_6$ alkoxy, amino and trifluoromethyl.

Halo means fluoro, chloro, bromo or iodo.

The compounds (I) are useful as synthetic intermediates in the manufacture of the antibiotics of EP-B-0413455 as explained in WO-A-93/18001.

WO-A-93/18001 describes a process for preparing a compound of formula (I) by reaction of a compound of formula (II):

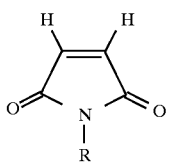

with a halonitromethane in the presence of a base, R being as defined for formula (I).

Example 1 of that application describes the preparation of 1α, 5α, 6α-3-benzyl-6-nitro-2,4-dioxo-3-azabicyclo [3.1.0] hexane by adding a solution of the base DBU (1,8-diazabicyclo [5.4.0] undec-7-ene) in toluene dropwise to a mixture of N-benzylmaleimide and bromonitromethane in toluene. However the yield of the end product isolated was only 17%. In terms of grams of activity, the yield would have been less than 17%.

U.S. patent application Ser. No. 08/181942 describes the use of 1,2-dimethyl-1,4,5,6-tetrahydropyrimidine (DMTHP) as the base in that process and the isolated yield was 26.7% (less in terms of grams of activity).

It has now been established that, when a quaternary ammonium fluoride is used as the base, very significant improvements in the yield of (I) are obtained.

Thus the present invention provides a process for preparing a compound of formula (I):

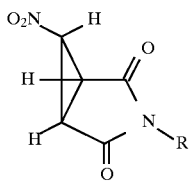

wherein R is $C_1$–$C_6$ alkyl, $C_3$–$C_6$ cycloalkyl or benzyl, and wherein the phenyl moiety of said benzyl group is optionally substituted with one or two substituents each independently selected from halo, nitro, $C_1$–$C_6$ alkyl, $C_1$–$C_6$ alkoxy, amino and trifluoromethyl, which comprises treating a solution of a compound of the formula (II):

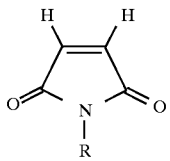

wherein R is as defined for formula (I), and a halonitromethane in a first organic solvent, with a quaternary ammonium fluoride of formula (III):

$$R^1R^2R^3R^4N^{\oplus} \ F^{\ominus} \quad \text{(III)}$$

wherein $R^1$, $R^2$, $R^3$ and $R^4$ are each independently selected from $C_1$–$C_8$ alkyl and benzyl, optionally in solution in a second organic solvent.

Preferably R is $C_1$–$C_6$ alkyl or benzyl.

More preferably R is benzyl.

Preferably the halonitromethane is chloronitromethane or bromonitromethane.

More preferably the halonitromethane is bromonitromethane.

Preferably $R^1$, $R^2$, $R^3$ and $R^4$ are each independently selected from methyl, ethyl, n-propyl, n-butyl and benzyl.

More preferably each of $R^1$, $R^2$, $R^3$ and $R^4$ is n-butyl.

Preferably the compound of formula (II) and the halonitromethane are used in a molar ratio of from 1:1 to 1:1.50.

More preferably the molar ratio is from 1:1.40 to 1:1.45.

Suitable said first and second organic solvents may be the same or different and independently selected from, for example, benzene, toluene, xylene, acetone, tetrahydrofuran, 1,2-dimethoxyethane, diglyme, 1,4-dioxan, acetonitrile, dimethylformamide and dimethylacetamide.

Typically, a solution of the compound of formula (III) is added dropwise to a solution of the compound of formula (II) and the halonitromethane, e.g. over a period of 0.5 to 1.5 hours depending on the scale of the reaction.

In one preferred aspect the first organic solvent is toluene and the second organic solvent is tetrahydrofuran.

The process is preferably conducted at a temperature of from −5 to 25° C.

More preferably it is conducted at from 0° to 10° C.

Most preferably it is conducted at from 4° to 60° C.

The following Example illustrates the typical yield of (I) obtainable by the process of the present invention.

High performance liquid chromatography (HPLC) method.

| | |
|---|---|
| Column: | Waters "Novapak" C18, 15 cm × 3.9 mm i.d. |
| Mobile phase: | 0.02M aqueous sodium dihydrogen phosphate:acetonitrile (60:40). |
| Flow rate: | 1.0 ml/min. |
| UV detection: | 220 nm. |
| Approximate retention times: | |
| bromonitromethane | 1.88 min. |
| N-benzylmaleimide | 3.47 min. |
| title compound | 4.59 min. |

$^1$H Nuclear magnetic resonance (NMR) spectra were recorded using a Varian Unity 300 spectrometer and were in all cases consistent with the proposed structure. Chemical shifts (δ) are given in parts-per-million downfield from tetramethylsilane.

Room temperature means 20° to 25° C.

EXAMPLE

1α. 5α. 6α-3-Benzyl-6-nitro-2.4-dioxo-3-azabicyclo[3.1.0]hexane.

A mixture of 13X molecular sieve powder (75.0 g) and toluene (450 ml) was stirred at room temperature until the exothermic reaction had subsided, then N-benzylmaleimide (18.7 g, 0.100 mol) and bromonitromethane (20.0 g, 0.143 mol) were added. The resulting mixture was cooled to 5° C. and then a 1M solution of tetra-n-butylammonium fluoride in tetrahydrofuran (150 ml, 0.150 mol) added dropwise over 1 hour whilst maintaining the reaction temperature at 4° to 6° C. The reaction mixture was stirred at 5° C. for a further 0.5 hour, when HPLC analysis showed that the reaction was essentially complete.

Celite (trade mark) (50 g) was added to the mixture and then the solvent (ca. 200 ml) exchanged with toluene by constant volume distillation whilst ensuring that the temperature was maintained below 40° C. The resulting slurry was allowed to cool to room temperature, filtered and the solid thus obtained then washed with toluene (3×250 ml). The combined filtrate and washings were washed sequentially with 4M hydrochloric acid (3×75 ml) and demineralised water (75 ml), then clarified by treatment with activated carbon (2.0 g) at 50° to 60° C. for 1 hour and filtration at 30° C. The clear orange filtrate was concentrated under reduced pressure to a volume of ca. 80 ml and the resulting slurry heated under gentle reflux (ca.110° C.) to afford a clear reddish orange solution which was allowed to cool to 35° C. over 45 minutes. Crystallisation occurred readily on seeding and the product was granulated for 2 hours at from -5° to 3° C., collected by filtration, washed with ice-cold toluene (20 ml) and dried under vacuum at 35° C. to furnish the title compound (11.16 g, 45.3%) as a pale cream crystalline solid, m.p. 116°-117° C. δ (CDCl₃):3.34 (s, 2H), 4.46 (s, 1H), 4.53 (s, 2H), 7.30 (s, 5H).

I claim:

1. A process for preparing a compound of formula (I):

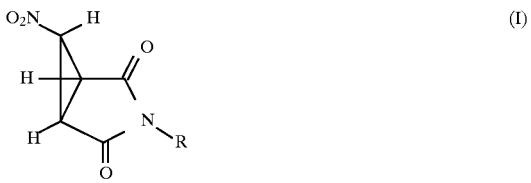

wherein R is $C_1$–$C_6$ alkyl, $C_3$–$C_6$ cycloalkyl or benzyl, and wherein the phenyl moiety of said benzyl group is optionally substituted with one or two substituents each independently selected from halo, nitro, $C_1$–$C_6$ alkyl, $C_1$–$C_6$ alkoxy, amino and trifluoromethyl, which comprises treating a solution of a compound of formula (II):

wherein R is as defined for formula (I), and a halonitromethane in a first organic solvent, with a quaternary ammonium fluoride of formula (III):

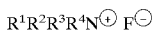

wherein $R^1, R^2, R^3$ and $R^4$ are each independently selected from $C_1$–$C_8$ alkyl and benzyl, optionally in solution in a second organic solvent.

2. A process according to claim 1 wherein R is $C_1$–$C_6$ alkyl or benzyl.

3. A process according to claim 2 wherein R is benzyl.

4. A process according to claims 1 wherein the halonitromethane is chloronitromethane or bromonitromethane.

5. A process according to claim 4 wherein the halonitromethane is bromonitromethane.

6. A process according to claim 1 wherein $R^1, R^2, R^3$ and $R^4$ are each independently selected from methyl, ethyl, n-propyl, n-butyl and benzyl.

7. A process according to claim 6 wherein each of $R^1, R^2, R^3$ and $R^4$ is n-butyl.

8. A process according to claim 1 to wherein the compound of formula (II) and the halonitromethane are used in a molar ratio of from 1:1 to 1:1.50.

9. A process according to claim 8 wherein the molar ratio is from 1:1.40 to 1:1.45.

10. A process according to claim 1 wherein the said first and second organic solvents may be the same or different and independently selected from benzene, toluene, xylene, acetone, tetrahydrofuran, 1,2-dimethoxyethane, diglyme, 1,4-dioxan, acetonitrile, dimethylformamide and dimethylacetamide.

11. A process according to claim 10 wherein the first organic solvent is toluene and the second organic solvent is tetrahydrofuran.

12. A process according to claim 1 to which is conducted at a temperature of from -5° to 25° C.

13. A process according to claim 12 which is conducted at from 0° to 10° C.

14. A process according to claim 13 which is conducted at from 4° to 6° C.

15. A process according to claim 1 wherein the solution of the compound of formula (III) is added dropwise to the solution of the compound of formula (II) and the halonitromethane.

16. The process according to claim 3 wherein said halonitromethane is selected from bromonitomethane and chloronitromethane, each of $R^1, R^2, R^3$ and $R^4$ is n-butyl, the molar ratio of the compound of the formula (II) to halonitromethane is from 1:1 to 1:1.50, the first solvent is toluene and the second solvent is tetrahydrofuran and the temperature of the reaction is from -5° to 25° C.

17. The process according to claim 16 wherein said halonitromethane is bromonitromethane.

18. The process according to claim 17 wherein the molar ratio of the compound of the formula (II) to halonitromethane is from 1:1.40 to 1:1.45.

19. The process according to claim 18 wherein the temperature of the reaction is from 0° to 10° C.

20. The process according to claim 19 wherein the temperature of the reaction is from 4° to 6° C.

* * * * *